US007534873B2

(12) United States Patent
Zon et al.

(10) Patent No.: US 7,534,873 B2
(45) Date of Patent: May 19, 2009

(54) METHOD AND MATERIALS FOR QUATERNARY AMINE CATALYZED BISULFITE CONVERSION OF CYTOSINE TO URACIL

(75) Inventors: Gerald Zon, San Carlos, CA (US); Victoria L. Boyd, San Carlos, CA (US)

(73) Assignee: Applied Biosystems, LLC, Foster City, CA (US)

(*) Notice: Subject to any disclaimer, the term of this patent is extended or adjusted under 35 U.S.C. 154(b) by 600 days.

(21) Appl. No.: 10/926,528

(22) Filed: Aug. 26, 2004

(65) Prior Publication Data

US 2005/0089898 A1    Apr. 28, 2005

Related U.S. Application Data

(60) Provisional application No. 60/523,054, filed on Nov. 17, 2003, provisional application No. 60/499,106, filed on Aug. 29, 2003.

(51) Int. Cl.
*C07H 21/02* (2006.01)
*C07H 21/04* (2006.01)

(52) U.S. Cl. .................................................. 536/23.1
(58) Field of Classification Search .................. 435/6
See application file for complete search history.

(56) References Cited

U.S. PATENT DOCUMENTS

| | | | |
|---|---|---|---|
| 6,214,556 B1 | 4/2001 | Olek et al. | |
| 6,251,594 B1 | 6/2001 | Gonzalgo et al. | |
| 6,277,603 B1* | 8/2001 | Cook | 435/91.1 |
| 6,331,393 B1 | 12/2001 | Laird et al. | |
| 6,511,810 B2 | 1/2003 | Bi et al. | |
| 7,262,013 B2 | 8/2007 | Boyd et al. | |
| 2004/0121359 A1 | 6/2004 | Berlin | |
| 2004/0152080 A1 | 8/2004 | Berlin et al. | |
| 2004/0241704 A1* | 12/2004 | Markert-Hahn et al. | 435/6 |
| 2005/0095623 A1 | 5/2005 | Zon et al. | |
| 2005/0153308 A1 | 7/2005 | Zon et al. | |
| 2006/0063189 A1 | 3/2006 | Zon | |

FOREIGN PATENT DOCUMENTS

| | | |
|---|---|---|
| EP | 1394173 A1 | 3/2004 |
| WO | WO02/30944 | 4/2002 |
| WO | WO 2004/067545 A | 8/2004 |
| WO | WO 2005/021563 A | 3/2005 |

OTHER PUBLICATIONS

Nandi et. al. Macromol. Rapid. Commun. 20(11), 582-585, (1999).*
U.S. Appl. No. 60/499,113, filed Aug. 29, 2003, Zon.
U.S. Appl. No. 60/520,942, filed Nov. 17, 2003, Zon.
U.S. Appl. No. 60/499,106, filed Aug. 29, 2003, Zon.
U.S. Appl. No. 60/523,054, filed Nov. 17, 2003, Zon.
U.S. Appl. No. 60/499,082, filed Aug. 29, 2003, Zon.
U.S. Appl. No. 60/523,056, filed Nov. 17, 2003, Zon.
U.S. Appl. No. 60/498,996, filed Aug. 29, 2003, Zon.
U.S. Appl. No. 60/520,941, filed Nov. 17, 2003, Zon.

Shapiro and Klein, "Reactions of Cytosine Derivatives With Acidic Buffer Solutions", Biochemistry, vol. 6, No. 11, Nov. 1967, pp. 3576-3582.
Shapiro et al., "Reactions of Uracil and Cytosine Derivatives With Sodium Bisulfite. A Specific Deamination Method", Journal of the American Chemical Society/92:2/Jan. 28, 1970.
Hayatsu et al., "Reaction of Sodium Bisulfite With Uracil, Cytosine, and Their Derivatives", Biochemistry, vol. 9, No. 14, 1970, pp. 2858-2865.
Shapiro and Weisgras, "Bisulfite-Catalyzed Transamination of Cytosine and Cytidine", Biochemical and Biophysical Research Communications, vol. 40, No. 4, 1970, pp. 839-843.
Shapiro et al., "Nucleic Acid Reactivity and Conformation", The Journal of Biological Chemistry, vol. 248, No. 11, Issue of Jun. 10, pp. 4060-4064, 1973.
Shapiro et al., "Deamination of Cytosine Derivatives by Bisulfite. Mechanism of the Reaction", Journal of the American Chemical Society/96:3/Feb. 6, 1974.
Hikoya Hayatsu, "Bisulfite Modification of Nucleic Acids and Their Constituents", Prog Nucleic Acid Res Mol Biol, 1976, 16 75-124.
Wang et al., "Comparison of Bisulfite Modification of 5-Methyldeoxycytidine and Deoxycytidine Residues" Nucleic Acids Research, vol. 8, No. 20, 1989, pp. 4776-4790.
Miller and Cushman, "Selective Modification of Cytosines in Oligodeoxyribonucleotides", Bioconjugate Chem 1992, 3, 74-79.
Frommer et al., "A Genomic Sequencing Protocol That Yields a Positive Display of 5-Methylcytosine Residues in Individual DNA Strands", Proc. Natl. Acad. Sci. USA, vol. 89, pp. 1827-1831, Mar. 1992, Genetics.
Kumar et al., "Immunoaffinity Chromatography to Isolate Methylated DNA Using Immobilized Anti-5 Methyl Cytosine Antibody", Biotechnology Techniques, vol. 5, No. 6, 469-470 (1991).
Molander et al., "Bisulfite Ion-Catalyzed Transamination of Cytosine Residues With a, w-Alkanediamines: The Effect of Chain Length on the Reaction Kinetics", Bioconjugate Chem. 1993, 4, 362-365.
Clark et al., "High Sensitivity Mapping of methylated Cytosines", 2990-2997, Nucleic Acids Research, 1994, vol. 22, No. 15.

(Continued)

*Primary Examiner*—Shaojia Anna Jiang
*Assistant Examiner*—Eric S Olson
(74) *Attorney, Agent, or Firm*—Michael A. Patané; Shirley A. Récipon

(57) ABSTRACT

The invention provides methods and materials for the conversion of cytosine to uracil. A nucleic acid, such a gDNA, is reacted with bisulfate, such as magnesium bisulfite, in the presence of a quaternary amine catalyst. Examples of suitable quaternary amine catalysts include but are not limited to quaternary ammonium compounds, quaternary alkyl ammonium salts, quaternary alkyl ammonium halides, quaternary methyl ammonium bromide, quaternary ammonium chloride, tetraethylammonium hydroxide, tetraethylammonium chloride, tetrabutylammonium chloride, tetrabutylammonium bromide. The invention also contemplates kits of pre-measured ingredients for carrying out the methods of the invention either on an individual sample or on a plurality of samples.

23 Claims, No Drawings

OTHER PUBLICATIONS

Paul and Clark, "Cytosine Methylation: Quantitation by Automated Genomic Sequencing and GENESCAN™ Analysis", BioTechniques 21:126-133 (Jul. 1996).

Olek et al., "A Modified and Improved Method for Bisulphite Based Cytosine Methylation Analysis", 5064-5066, Nucleic Acids Research, 1996, vol. 24, No. 24.

Herman et al., "Methylation-specific PCR: A Novel PCR Assay for Methylation Status of CpG Islands", Proc. Natl. Acad. Sci. USA, vol. 93, pp. 9821-9826, Sep. 1996, Medical Sciences.

Rein et al., "Active Mammalian Replication Origins Are Associated With a High-Density Cluster of $^m$CpG Dinulceotides", Molecular and Cellular Biology, Jan. 1997, vol. 17, No. 1, p. 416-426.

Paulin et al., "Urea Improves Efficiency of Bisulphite-Mediated Sequencing of 5'-Methylcytosine in Genomic DNA", Nucleic Acids Research, 1998, vol. 26, No. 21, 5009-5010.

Warnecke et al., "Bisulfite Sequencing in Preimplantation Embryos: DNA Methylation Profile of the Upstream Region of the Mouse Imprinted H19 Gene", Genomics 51, 182-190 (1990), Article No. GE985371.

Oakeley, E., et al., "Quantification of 5-Methylcytosine in DNA by the Chloroacetaldehyde Reaction", BioTechniques 27:744-752 (Oct. 1999).

Oakeley, "DNA Methylation Analysis: A Review of Current Methodologies", Pharmacology & Therapeutics 84 (1999) 389-400.

Thomassin et al., "Identification of 5-Methylcytosine in Complex Genomes", Methods, 19, 465-475 (1999).

Grunau et al., "Bisulfite Genomic Sequencing: Systematic Investigation of Critical Experimental Parameters", Nucleic Acids Research, 2001, vol. 29, No. 13, e65.

Kerjean et al., "Bisulfite Genomic Sequencing of Microdissected Cells", Nucleic Acids Research, 2001, vol. 29, No. 21 e106.

Trinh et al., "DNA Methylation Analysis by MethyLight Technology", Methods 25, 456-462 (2001).

Balog et al., "Parallel Assessment of CpG Methylation by Two-Color Hybridization With Oligonucleotide Arrays", Analytical Biochemistry, 309 (2002) 301-310.

Rand et al., "Conversion-Specific Detection of DNA Methylation using Real-Time Polymerase Chain Reaction (ConLight-MSP) to Avoid False Positives", Methods, 27 (2002), 114-120.

Frigola et al., "Methylome Profiling of Cancer Cells by Amplification of Inter-Methylated Sites (AIMS)", Nucleic Acids Research, 2002, vol. 30, No. 7 e28.

Fraga and Esteller, "DNA Methylation: A Profile of Methods and Applications", BioTechniques 33:632-649 (Sep. 2002).

El-Maarri et al., "A Rapid, Quantitative, Non-Radioactive Bisulfite-SNuPE-IP RP HPLC Assay for Methylation Analysis at Specific CpG Sites", Nucleic Acids Research, 2002, vol. 30, No. 6, e25.

Li and Dahiya, "MethPrimer: Designing Primers for Methylation PCRs", Bioinformatics, vol. 18, No. 11, 2002, pp. 1427-1431.

Okamoto et al., "Site-Specific Discrimination of Cytosine and 5-Methylcytosine in Duplex DNA by Peptide Nucleic Acids", JACS Communications (Apr. 10, 2002).

Friso et al., "A Method to Assess Genomic DNA Methylation Using High-Performance Liquid Chromatography/Electrospray Ionization Mass Spectrometry", Anal. Chem. 2002, 74, 4526-4531.

Mills and Ramsahoye, "DNA Methylation Protocols", Methods in Molecular Biology, vol. 200, (2002).

Ushijima et al., "Fidelity of the Methylation Pattern and Its Variation in the Genome", Genome Research, (2003), pp. 868-874.

"EZ DNA Methylation Kit™", Instructions, Zymo Research.

Humeny, A.., et al., Detection and analysis of enzymatic DNA methylation of oligonucleotide substrates by matrix-assisted laser desorption ionization time-of-flight mass spectrometry, Anal. Biochem. 313 (2003) 160-166.

Kinoshita, H., et al., Screening hypermethylated regions by methylation-sensitive single-strand conformational polymorphism, Anal. Biochem. 278 (2000) 165-169.

Kubareva et al., "Dtermination of Methylation Site of DNA-Methyl-Transferase Nylax by a Hybrid Method," Biotechniques, Eaton Publishing, Natick, U.S., vol. 33, No. 3, Sep. 2002, pp. 526-531.

Boyd, et al., Bisulfite conversation of genomic DNA for methylation analysis: protocol simplification with higher recovery applicable to limited samples and increased throughput, Analytical Biochemistry, Academic Press, San Diego, CA, U.S., vol. 326, No. 2, Mar. 15, 2004, pp. 278-280.

Komiyama, et al., "Catalysis of diethylenetriamine for bisulfite-induced deamination of cytosine in oligodeoxyribonucleotides," Tetrahedron Letters (1994) 35(44): 8185-8188.

International Search Report mailed Jan. 31, 2005 from International Application No. PCT/US2004/028089, published as WO/2005/021803.

International Search Report mailed May 18, 2005 from International Application No. PCT/US04/28070, published as WO/2005/021778.

International Search Report mailed Apr. 15, 2005 from International Application No. PCT/US04/27992, published as WO/2005/021563.

International Search Report mailed Jun. 27, 2005 from International Application No. PCT/US2004/028032, published as WO/2005/021802.

EZ DNA Methylation Kit™, Instructions, Zymo Research, Mar. 11, 2003.

Dr. Alex Schumacher, "Schumacher's Guide for: Bisulfite Conversion of DNA for Methylation Fine-Mapping," *Schumacher's Guide #1: Bisulfite Conversion of DNA for Methylation Profiling*, Version 1.a, Jan. 25, 2007, pp. 1-6.

* cited by examiner

METHOD AND MATERIALS FOR QUATERNARY AMINE CATALYZED BISULFITE CONVERSION OF CYTOSINE TO URACIL This application claims benefit of priority to U.S. Provisional Application Ser. Nos. 60/499,106 filed Aug. 29, 2003 and No. 60/523,054 filed Nov. 17, 2003, each of which is hereby incorporated by reference.

FIELD

The invention relates generally to methods and materials for the conversion of cytosine to uracil.

BACKGROUND

Assessment of methylation of DNA is useful in many research, diagnostic, medical, forensic, and industrial fields. Key to this assessment is converting cytosine, but not methylcytosine, to uracil, but not thymine. One basic method for such conversion, employing sodium bisulfite, is well known. Over the years, the method has been improved in attempts to overcome disadvantages that include tedious procedures, lengthy reaction times, and DNA degradation. The most commonly used protocol is taught by J. Herman, *Proc. Natl. Acad. Sci.* 93, 9821-26 (1996), incorporated herein by reference in its entirety. This method involves denaturation, reaction with sodium bisulfite in the presence of hydroquinone, and subsequent completion of the modification by treatment with NaOH. Despite the attempts to improve the protocol, current procedures require pre-denaturation of the genomic DNA (gDNA) to single stranded DNA (ssDNA), preparation of fresh solutions of sodium bisulfite ($NaHSO_3$), typically about 3M, and inclusion of an anti-oxidant (e.g., hydroquinone). The protocol also requires long reaction times and tedious clean-up procedures.

In addition, the currently employed sodium bisulfite protocols are plagued by reports of incomplete conversion, irreproducible results, and other problems. In some cases, the reaction can result in significant DNA degradation (reportedly as high as 96%), making it difficult to obtain enough sample for further analysis. See. S. J. Clark et al. *Nucleic Acid Research* 2001, 29 no. 13, e65. Given the importance of assessment of DNA methylation, it can be seen that there is a need for improved methodologies for conversion of cytosine to uracil.

It has been discovered that bisulfite methods that employ magnesium bisulfite, polyamine compounds, and/or quaternary amine compounds provide useful alternatives to sodium bisulfite conversion reactions. These discoveries are the subjects of co-owned applications entitled "Method And Materials For Polyamine Catalyzed Bisulfite Conversion Of Cytosine To Uracil" (U.S. application Ser. No. 10/926,530, filed Aug. 26, 2004 claiming priority to U.S. application Ser. No. 60/499,113 filed Aug. 29, 2003, and also application Ser. No. 60/499,113 having the same title and filed Nov. 17, 2003), "Method And Materials For Quaternary Amine Catalyzed Bisulfite Conversion Of Cytosine To Uracil" (U.S. application Ser. No. 10/926,528, filed Aug. 26, 2004 claiming priority to U.S. application Ser. No. 60/499,106 filed Aug. 29, 2003, and also application Ser. No. 60/523,054 having the same title and filed Nov. 17, 2003) and "Method and Materials for Bisulfite Conversion of Cytosine to Uracil" (U.S. application Ser. No. 10/926,531, filed Aug. 26, 2004 claiming priority to U.S. application Ser. No. 60/499,082 filed Aug. 29, 2003, and also application Ser. No. 60/523,056 having the same title and filed Nov. 17, 2003), all of which are hereby incorporated by reference in their entirety. Improvements in clean-up procedures associated with conversion of cytosine to uracil are also the subject of co-owned applications entitled "Improved Bisulfite Method" (U.S. application Ser. No. 10/926,534, filed Aug. 26, 2004 claiming priority to U.S. application Ser. No. 60/498,996 filed Aug. 29, 2003, and also application Ser. No. 60/520,941 having the same title and filed Nov. 17, 2003) now U.S. Pat. No. 7,262,013, issued Aug. 28, 2007, all of which are hereby incorporated by reference in their entirety.

SUMMARY

In certain embodiments of the invention, the invention comprises methods of specifically converting cytosine to uracil by using a catalyzed bisulfite reaction.

In some embodiments, the present invention provides methods for the conversion of cytosine to uracil in a nucleic acid comprising the steps of:

reacting a nucleic acid comprising at least one cytosine nucleobase with bisulfite ion in the presence of a quaternary amine catalyst.

In some embodiments, the quaternary amine comprises a compound having Formula I:

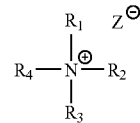

Formula I or a derivative thereof, wherein:

$R_1$, $R_2$, $R_3$ and $R_4$ are each independently alkyl, preferably $C_1$-$C_4$ alkyl; and $Z^\ominus$ is selected from the halides and $OH^-$.

In some embodiments, $R_1$, $R_2$, $R_3$ and $R_4$ are identical.

In some embodiments of the invention, the quaternary amine catalyst comprises a quaternary ammonium compound, or a derivative thereof. In further embodiments, the quaternary amine catalyst comprises a quaternary alkyl ammonium salt. In yet further embodiments, the quaternary amine catalyst comprises a quaternary alkyl ammonium halide, for example a quaternary ammonium chloride or a quaternary ammonium bromide. In some embodiments, the quaternary amine catalyst comprises at least one of quaternary methyl ammonium bromide, tetraethylammonium hydroxide, tetraethylammonium chloride, tetrabutylammonium chloride and tetrabutylammonium bromide.

In some embodiments, the reaction of the nucleic acid and bisulfite ion is performed in a solution containing bisulfite ion, such as magnesium bisulfite, in a concentration of from about 0.5M to about 2.5M. In further embodiments, the solution contains bisulfite ion, such as magnesium bisulfite, in a concentration of from about 1M to about 2M.

In some embodiments, the magnesium bisulfite is present at a concentration of at least about 1M.

Also provided are methods for the conversion of cytosine to uracil comprising the steps of reacting a DNA sample in solution with a bisulfite salt and quaternary amine catalyst as described above, wherein the concentration of the bisulfite salt is from about 0.5M to about 2M. In further embodiments, the concentration of the bisulfite salt is about 1.3M.

In some embodiments of the methods of the invention, the reaction is performed at a temperature from about 40 to about 60 degrees, such as about 50 degrees, for about 4 to about 15 hours. In further embodiments of the methods of the invention, the nucleic acid is gDNA.

Also provided in accordance with the present invention are kits for use in conversion of cytosine to uracil comprising magnesium bisulfite; and a quaternary amine catalyst as described above. In some embodiments of such kits, the magnesium bisulfite is provided as an approximately 2M magnesium bisulfite solution. In further embodiments of the kits of the invention, the quaternary amine catalyst comprises tetraethylammonium hydroxide. In some embodiments, the kits further comprise reagents for sequencing and/or amplification (e.g., by PCR), for example a polymerase and one or more primers. In some embodiments, the kits contain premeasured materials useful in various embodiments of the methods of the invention.

In some embodiments, the methylation status of one or more cytosines in the target nucleic acid(s) can be determined by any suitable method. Typically, methylation status can be determined by measuring the presence or relative amount of uracil at a nucleotide position that was previously non-methylated cytosine, and was converted to uracil by the bisulfite treatment. If desired, the presence or relative amount of residual cytosine at the same nucleotide position (indicating the presence of methylcytosine) can be measured for comparison with the amount of uracil, to determine the degree of methylation at the particular nucleotide position. Appropriate control experiments can also be performed to correct for incomplete transformation of cytosine to uracil, if desired.

The presence or amount of uracil and/or methylcytosine at a particular nucleotide position can be measured by any suitable method, such as DNA sequencing (e.g., by the Sanger method or Maxam-Gilbert method or subsequent embodiments thereof (e.g., using dye-labeled terminators or dye-labeled primers, such as discussed in WO 02/30944 and by Ansorge et al. DNA Sequencing Strategies—Automated and Advanced Approaches, John Wiley & Sons, New York, 1997)), PCR (e.g., primer-specific PCR), oligonucleotide ligation assay (OLA) or other ligation-dependent techniques (e.g., see U.S. Pat. No. 6,511,810 and references cited therein), single base extension (over the potential methylation site), mass spectrometry, real time PCR (e.g., using labeled probes that are complementary to C and or U), microarrays comprising sequence specific probes, etc. Various exemplary techniques are also described by Kirk et al., Nucl. Acids Res., 30:3295-3311 (2002).

DETAILED DESCRIPTION

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Definitions

As used herein, the term "alkyl" is intended to mean saturated hydrocarbon species, including without limitation straight, branched chain and cyclic hydrocarbons, for example, methyl, ethyl, n-propyl, isopropyl, n-butyl, sec-butyl, t-butyl, n-pentyl, sec-pentyl, t-pentyl, neopentyl, cyclopropyl, cyclobutyl, cyclopentyl, and cyclohexyl groups.

As used herein, the term "EXO/SAP" denotes a mixture of exonuclease I (EXO) and shrimp alkaline phophatase (SAP).

As used herein, the term "gDNA" refers to genomic DNA.

Bisulfite ion has its accustomed meaning of $HSO_3^-$. Typically, bisulfite is used as an aqueous solution of a bisulfite salt, for example magnesium bisulfite, which has the formula $Mg(HSO_3)_2$, and sodium bisulfite, which has the formula $NaHSO_3$.

The term "PCR" is intended to denote polymerase chain reaction, as is well known in the art. The term "MSP" denotes methylation specific PCR, such as described by J. Herman, Proc. Natl. Acad. Sci. 93, 9821-26 (1996), and modified as discussed herein.

As used herein, the term "nucleic acid" includes, for example, nucleobase-containing polymeric compounds, including naturally occurring and non-naturally occurring forms thereof, for example and without limitation, genomic DNA, cDNA, hnRNA, mRNA, rRNA, tRNA, fragmented nucleic acids, nucleic acids obtained from subcellular organelles such as mitochondria or chloroplasts, and nucleic acids obtained from microorganisms, or DNA or RNA viruses that may be present on or in a biological sample.

The term "quaternary amine compound" or "quaternary amine" is intended to include, without limitation, compounds containing a tetra-substituted nitrogen atom, and the salts and hydroxides of such compounds. Examples of quaternary amine compounds include, without limitation, quaternary alkyl ammonium compounds, for example quaternary alkyl ammonium halides. Thus, quaternary amine compounds include quaternary alkyl ammonium chlorides such as quaternary methyl ammonium bromide, quaternary alkyl ammonium bromides, quaternary ammonium chlorides, tetraethylammonium hydroxide, tetraethylammonium chloride, tetrabutylammonium chloride, tetrabutylammonium bromide, and the like.

The term "ssDNA" refers to single stranded DNA, resulting typically, but not exclusively, from denaturing double stranded DNA ("dsDNA").

The term "TE buffer" refers to the well-known buffering solution of 10 mM TRIS-HCl and 1 mM EDTA that is typically used in analysis of nucleic acids.

The term "triamine" refers to compounds having three amino groups, including but not limited to diethylene triamine (DETA), guanidine HCl, tetramethyl guanidine, and the like.

The term "nucleic acid sample" is intended to denote a sample (e.g., a composition, mixture, suspension or solution) that contains at least one nucleic acid.

Unless otherwise specified, reference herein to cytosine refers to unmethylated cytosine and conversion refers to specific conversion of unmethylated cytosine to uracil.

All reported temperatures are in degrees Celsius unless stated otherwise.

In some embodiments, the present invention provides methods of converting cytosine to uracil in a nucleic acid sample by using a catalyzed bisulfite reaction. The methods of the present invention can provide significant benefits.

The nucleic acid samples may be obtained by any conventional collection and purification process prior to use in the methods of the invention. The examples discussed below used commercially available sample lines (e.g. from Coriell or Intergen) of known methylation status, to assess the viability of the methods.

Typically, the product of the reaction between the nucleic acid and bisulfite is reacted with a base to complete the conversion of cytosine to uracil. One typical base is NaOH. In some embodiments the methods herein further comprise the step of purifying the bisulfite-reacted nucleic acid prior to treatment with base. In some further embodiments, the methods further comprise the step of analyzing the product of the bisulfite conversion reaction, for example by mass spectrometry, to confirm completion of the bisulfite conversion reaction.

Typical protocols in the art require the use of 3M sodium bisulfite, long reaction times of up to 16 hours, and the presence of an antioxidant. Because of the relatively high salt concentration, the low pH of the reaction and the long reaction times, the DNA can be degraded. Additionally, the ssDNA resulting from the gDNA is difficult to purify away from the high salt concentration used in the reaction. In addition, it is typically necessary to remove most of the bisulfite, which interferes with subsequent enzymatic reactions, for example those of PCR protocols. Prior procedures also require freshly prepared solutions of bisulfite and antioxidant (typically hydroquinone).

Embodiments of the methods of the present invention may overcome one or more disadvantages of prior methods. For example, it has been discovered in accordance with some embodiments of the present invention that the reaction of a nucleic acid of interest with bisulfite ion, such as magnesium bisulfite, in the presence of a quaternary amine in accordance with the methods disclosed herein afford faster reaction times. In addition, because the reaction time is faster, less oxidation may occur. Thus, the presently disclosed methods do not require addition of an antioxidant such as hydroquinone. Additionally, magnesium bisulfite solution at 1M concentration may remain acidic in the presence of effective concentrations of polyamine catalyst (for example 0.1M DETA), whereas the corresponding solution of sodium bisulfite salt does not. Thus, methods of the invention can employ bisulfite concentrations that are significantly less than the methods known in the art, thereby affording facilitated sample preparation for PCR. Moreover, it has been discovered herein that stock magnesium bisulfite solutions can be employed, thus eliminating the need to freshly prepare those solutions. Finally, methods of the invention reduce or eliminate the need for a separate pre-denaturation step, and can be performed in a greatly reduced reaction volume. Thus, methods of the present invention can afford PCR yields similar to those of protocols previously known in the art, but with reduced preparation times, reaction times, and clean-up efforts.

Suitable counter-ions for the bisulfite compound may be monovalent or divalent. Examples of monovalent cations include, without limitation, sodium, lithium, potassium, ammonium, and tetraalkylammonium. Suitable divalent cations include, without limitation, magnesium, manganese, and calcium.

In certain embodiments, the invention comprises kits for carrying out the methods of the invention. In one embodiment, a kit of the invention includes pre-measured ingredients required for carrying out the bisulfite reaction, such as magnesium bisulfite and catalyst. In certain embodiments, the catalyst comprises tetraethylammonium hydroxide. In certain embodiments, the invention includes a kit containing pre-packaged materials sufficient to prepare multiple samples. In yet another embodiment, the materials will be pre-packaged with appropriate Eppendorf tubes or other reaction vessels, as appropriate.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The examples described herein are certain embodiments chosen to illustrate the invention. Applicant does not limit the invention to these embodiments. Rather, Applicant acknowledges that those reasonably skilled in the art will readily recognize additional variants that do not differ from the scope and spirit of the inventions disclosed herein.

EXAMPLES

In accordance with the present invention, it has been found that quaternary amines, such as tetraethylammonium hydroxide ($Et_4NOH$), are useful catalysts in the bisulfite conversion of cytosine to uracil in nucleic acid samples.

Methyl-Specific PCR Analysis

Each sample discussed herein was analyzed by methyl-specific PCR (MSP). MSP provides a relatively fast analysis method for methylation status of bisulfite-treated DNA samples, providing a yes/no answer. The method is based on using primer pair sets. One primer pair is designed to anneal/PCR amplify only if all cytosines were successfully converted to uracil, and the other primer pair in the set annealed/PCR amplified if the methylated cytosine (CpG cytosines only) were methylated, and therefore not converted to uracil.

The MSP pairs that amplify specific gene fragments, and the expected size of the amplicon, are the following:

for the p16 gene, unmethylated reaction (size 151):

```
                                          (SEQ ID NO:1)
5'-TTATTAGAGGGTGGGGTGGATTGT-3' (sense), (SEQ ID NO:2)
5'-CAACCCCAAACCACAACCATAA-3' (antisense);
``` methylated reaction (size 150):

```
                                          (SEQ ID NO:3)
5'-TTATTAGAGGGTGGGGCGGATCGC-3' (sense), (SEQ ID NO:4)
5'-GACCCCGAACCG-CGACCGTAA-3' (antisense);
``` for the MGMT gene, unmethylated reaction (93):

```
                                          (SEQ ID NO:5)
5'-TTTGTGTTTTGATGTTTGTAGGTTTTTGT-3' (sense), (SEQ ID NO:6)
5'-AACTCCACACTCTTCCAAAAACAAAACA-3' (antisense);
``` methylated reaction (81):

5'-TTTCGACGTTCGTAGGTTTTCGC-3' (sense), (SEQ ID NO:7)

5'-GCACTCTTCCGAAA-ACGAAACG-3' (antisense); (SEQ ID NO:8)

for the DAP-kinase gene, unmethylated reaction:

5'-GGAGGATAGTTGGATTGAGTTAATGTT-3' (sense), (SEQ ID NO:9)

5'-CAATCCCT-CCCAAACACCAA-3' (antisense); (SEQ ID NO:10)

methylated reaction:

5'-GGATAGTCGGATCGAGTTAACGTC-3' (sense), (SEQ ID NO:11)

5'-CCCTCCCAAACGCCG-3' (antisense); (SEQ ID NO:12)

for the MLH1 gene, unmethylated reaction (124):

5'-TTTTGATGTAGATGTTTTATTAGGGTTGT (sense) (SEQ ID NO:13)

5'-ACCACCTCATCATAACTACCCACA (antisense) (SEQ ID NO:14)

methylated reaction (115)

5'-ACGTAGACGTTTTATTAGGGTCGC (sense) (SEQ ID NO:15)

5'-CCTCATCGTAACTACCCGCG (antisense) (SEQ ID NO:16)

for the p15 gene, unmethylated reaction (154):

5'-TGTGATGTGTTTGTATTTTGTGGTT (sense) (SEQ ID NO:17)

5'-CCATACAATAACCAAACAACCAA (antisense) (SEQ ID NO:18)

methylated reaction (148)

5'-GCGTTCGTATTTTGCGGTT (sense) (SEQ ID NO:19)

5'-CGTACAATAACCGAACGACCGA (antisense) (SEQ ID NO:20)

The PCR recipe used to evaluate the samples was:

| 2X Taq Gold PCR Master Mix | 10 µL |
| Fwd primer (5 µM) | 1 µL |
| Rev primer (5 µM) | 1 µL |
| Bisulfite treated DNA | 0.5 µL |
| H2O | 7.5 µL |
| | 20 µL |

2×TaqGold PCR master mix is commercially available from Applied Biosystems. The forward and reverse primer sequences are those listed above.

The following thermal cycling schedule was used:

| 40 cycles | 95 deg 5 min |
| | 95 deg 30 sec |
| | 60 deg 45 sec |
| | 72 deg 1:00 min |
| | 4 deg forever |

One of the primers in each set was synthesized with a 5'FAM label. A 1 uL aliquot of the above PCR reaction was added to HiDi formamide with ROX 500 size standard added, and denatured by heating at 95° C. for 5 min. By using a FAM-labeled primer, the PCR amplicon was directly analyzed on an ABI PRISM® 310 Genetic Analyzer, with POP-4™ polymer, using run module "GS POP4 (1 mL) A" (reagents and instrument all from Applied Biosystems).

The presence of a PCR amplicon (i.e., a "peak") having the correct size as observed using the 310 Genetic Analyzer indicated a successful reaction. Additionally, the height or area of the peak could be used empirically to determine how much template (i.e., bisulfite-treated gDNA) was initially present. The bigger the peak, the more DNA was initially present.

The MSP-PCR product was then sometimes sequenced for further "resolution". DNA sequencing was by standard protocol and reagents from Applied Biosystems.

Prior to sequencing of the PCR amplicon, the primers and excess dNTPs used during the MSP-PCR were removed by treatment of a 4 µL aliquot of the PCR reaction with an equal volume mixture containing 2 Units each of Shrimp Alkaline Phosphatase (SAP) and exonuclease 1 (EXO) (USB Corporation, Cleveland, Ohio). The reaction was incubated at 37° C. for 1 hr, and then heat-denatured at 75° C. for 15 min. A 4 µL aliquot of the EXO/SAP reaction was added to a solution containing 1-4 µL of BigDye® Terminator v1.1 cycle sequencing reaction mix (Applied Biosystems), 2 µL of Big-Dye® Terminator v1.1 5× sequencing buffer, 2 µL of the reverse PCR primer (5 µM) (which did not have a FAM-label), and enough water for a final volume of 20 µL. Thermal cycling: 95° C./1 min, 50 cycles of 96° C./10 sec, 52° C./10 sec, 60° C./4 min, and stored at 4° C. The cycle-sequencing reaction products were purified by an Edge Biosystems Performa® 96-well plate, dried under vacuum, dissolved in 20 µL of HiDi Formamide and analyzed on an ABI PRISM® 3730 DNA Analyzer with KB basecaller or a 3700 DNA Analyzer.

General Protocol for Quaternary Amine Conversion

A basic protocol for the quaternary amine conversion reaction is set forth below for purposes of illustration. In an Eppendorf tube, or other suitable vessel, about 300 ng DNA, 10 µL water, 10 µL 20% Et$_4$NOH (to about 0.1 mM final concentration), and 85 µL magnesium bisulfite (to about 1.3M final concentration) are combined. The resulting mixture is incubated at about 50° C. for 4 to 15 hours, prior to purification and subsequent PCR of the treated product. Purification can be conducted by existing means, such as in accordance with the protocol of J. Herman, *DNAs* 93, 9821-26 (1996), incorporated herein by reference in its entirety, or with commercially available kits such as the Wizard DNA clean-up kit (available from Promega) or the EZ DNA Methylation Kit™ (available from Zymo Research).

A new purification method, which recovers the bisulfite-treated DNA very effectively, is the subject of the application entitled "Improved Bisulfite Method" (U.S. application Ser. No. 10/926,534, filed Aug. 26, 2004 claiming priority to U.S. application Ser. No. 60/498,996 filed Aug. 29, 2003, and also application Ser. No. 60/520,941 (5109P2) having the same title and filed concurrently herewith, now U.S. Pat. No. 7,262,013, issued Aug. 28, 2007), each of which is hereby incorporated by reference in its entirety.

In contrast with known sodium bisulfite conversion reaction protocols, all bisulfite conversion reactions disclosed herein were carried out without predenaturation, and without the inclusion of an antioxidant (e.g., hydroquinone), unless otherwise indicated.

The magnesium bisulfite used in the Examples described herein was purchased as a 2M $Mg(HSO_3)_2$ solution from Aldrich Chemical Co., Milwaukee, Wis. The pH of the solution was 2.6. The solution was used off-the-shelf, as purchased, and was not freshly prepared prior to each use.

Determination of Catalytic Effect of Quaternary Amines

Examples 1-3, shown in Table 1 below, show the catalytic effect of quaternary amine compounds.

TABLE 1

| Ex. 1 | Ex. 2 | Ex. 3 |
|---|---|---|
| 3 μL Coriell #NA09024C | 3 μL Coriell #NA09024C | 3 μL Coriell #NA09024C |
| — | 45 μL water | 35 μL water |
| 85 μL 2 M $Mg(HSO_3)_2$ | 85 μL 2 M $Mg(HSO_3)_2$ | 85 μL 2 M $Mg(HSO_3)_2$ |
| 45 μL TBAC (2 M) | 5.5 μL 2 M DETA | 10 μL 20% $Et_4NOH$ |

The resultant products were purified by standard methods (Wizard kit) and analyzed by MSP using the following MSP primer set: p15M, Dapk M, MgMt M, and p16M and four corresponding unmethylated templates: p15 U, Dapk U, MgMt U, and p16 U. The methylated primer pairs, p15M, Dapk M, MgMt M, and p16M were all negative, as expected, since the gDNA sample was not expected to be methylated. No product peak was expected or seen as with the p15M template. However, for the unmethylated gDNA samples, well-defined product peaks were seen in $Et_4NOH$ and TBAC catalyzed reactions when the unmethylated primer pairs were used in MSP analysis.

Effect of Antioxidant and Concentration of Quaternary Amine

Examples 5-8, shown below in Table 2, vary with respect to the presence or absence of antioxidant, and the identity and amount of quaternary amine.

Each of Examples 5-8 were incubated at 50° C. for four hours. The reaction mixture in example 8 immediately formed a large amount of precipitate, which remained even after incubation, and was excluded from further study. Example 7 had a non-interfering amount of precipitate and was retained in the study. After the four hour incubation, the remaining three samples were purified according to the new purification method referred to above, which employed a size-exclusion purification process. The process uses a Microcon 100 (Millipore) size-exclusion device. The sample and 200 μL of water were added to the Microcon 100 device, and the sample was then spun in the device at approximately 2800 RPM for about 8 minutes (as per manufacturer's recommendation). The resultant filtrate was removed. Two subsequent washes with about 300 μL water, each spun at about 2800 RPM for 8 minutes followed. After each, the filtrate was again removed. About 300 μL 0.1N NaOH was added and spun at approximately 2800 RPM for about 8 minutes. Again, the filtrate was removed. After addition of about 300 μL of water, the sample was spun in the device at 2800 RPM for about 6-8 minutes. The filtrate was removed and about 50 μL TE buffer (approximately pH 8) was added. After about 5 minutes it was inverted to collect the purified DNA sample in a centrifuge. Approximately 60 μL were collected.

The bisulfite-treated DNA was analyzed by MSP using the following MSP primer sets: p15 M, p15 U, Dapk M, Dapk U, Mgmt M, Mgmt U, p16 M, and p16 U. Hydroquinone did not appear to greatly enhance PCR yields. The $Et_4NOH$ sample displayed a far greater product peak than TBAC with or without hydroquinone. Only about 6 ng of bisulfite-treated gDNA was used per PCR. Prior experiments using the published purification protocol (Wizard resin) provided much less isolated DNA based on the amount required for successful PCR. These data support the use of quaternary amine, and specifically $Et_4NOH$, as a catalyst.

Reduced gDNA Concentration in $Et_4NOH$ Catalyzed Magnesium Bisulfite Reaction

The samples in Examples 9-12, shown in Table 3, demonstrate the bisulfite conversion of reduced amounts of DNA. These samples vary with respect to either the amount of DNA used, or reduced concentration of magnesium bisulfite/$Et_4NOH$.

TABLE 2

| Ex. 5 | Ex. 6 | Ex. 7 | Ex. 8 |
|---|---|---|---|
| 3 μL NA 13705 | 3 μL NA 13705 | 3 μL NA 13705 | 3 μL NA 13705 |
| 5.5 μL 2 M NaOH | 5.5 μL 2 M NaOH | 35 μL water | 35 μL water |
| 45 μL 2 M TBAC | 45 μL 2 M TBAC | 10 μL 20% $Et_4NOH$ | 20 μL 20% $Et_4NOH$ |
| incubate at 37° for 10–12 minutes | incubate at 37° for 10–12 minutes | | |
| 55 μL 2 M $Mg(HSO_3)_2$ | 30 μL Hydroquinone | 85 μL 2 M $Mg(HSO_3)_2$ | 60 μL 2 M $Mg(HSO_3)_2$ |
| — | 85 μL 2 M $Mg(HSO_3)_2$ | — | — |

TABLE 3

| Ex. 9 | Ex. 10 | Ex. 11 | Ex. 12 |
|---|---|---|---|
| 3 µL Coriell 13705 | 1 µL Coriell 13705 | 1 µL Coriell 13705 | 1 µL Coriell 13705 |
| 35 µL water | 35 µL water | 35 µL water | 35 µL water |
| 10 µL 20% Et$_4$NOH | 10 µL 20% Et$_4$NOH | 5 µL 20% Et$_4$NOH | 2.5 µL 20% Et$_4$NOH |
| 85 µL 2 M Mg(HSO$_3$)$_2$ | 85 µL 2 M Mg(HSO$_3$)$_2$ | 40 µL 2 M Mg(HSO$_3$)$_2$ | 85 µL 2 M Mg(HSO$_3$)$_2$ |
| ~1.3 M final | ~1.3 M final | ~1.0 M final | ~0.8 M final |

Example 9 (3 µL of Coriell) contained about 1 µg DNA, and Examples 10-12 (1 µL of Coriell) contains about 300 ng DNA. Each of these samples was allowed to react as previously discussed, at 50° C. for four hours. Subsequent to this incubation period, each was subject to the size-exclusion purification process discussed above, using the Microcon 100 device. The process differed from that previously discussed only in that slightly more water was used, and about 350 µL of 0.1M NaOH was used. Each was collected in about 50 µL TE buffer, and 1 µL was used in subsequent PCR. Surprisingly, the 300 ng sample at 1.3M magnesium bisulfite (Example 10) was observed to provide more PCR product than the 1 µg sample (Example 9).

Effect of Enzyme Concentration and Template (gDNA) Concentration in MSP

The same bisulfite-treated samples above, specifically, Ex. 9 and Ex. 10, were further analyzed by MSP under alternative conditions: (a) additional polymerase (TaqGold) and (b) less bisulfite-treated gDNA template. The MSP conditions are shown in Table 4, below.

TABLE 4

| Ex. 13 | Ex. 14 | Ex. 15 | Ex. 16 | Ex. 17 | Ex. 18 |
|---|---|---|---|---|---|
| Ex. 9 bisulfite-treated DNA with xs enzyme | Ex. 10 bisulfite-treated DNA with xs enzyme | NTC with xs enzyme | 1/10 of Ex. 9 bisulfite-treated DNA (0.6 ng/µL) | 1/20 of Ex. 9 bisulfite-treated DNA (0.3 ng/µL) | 1/30 of Ex. 9 bisulfite-treated DNA (0.2 ng/µL) |

Each PCR was prepared as described in the MSP analysis described elsewhere herein. MSP primer sets used were Mlh M, Mlh U, Dapk M, Dapk U, Mgmt M, Mgmt U, p16 M, and p16 U. When excess TaqGold polymerase was used, an additional 2 µL (2 units) was added to the reaction.

The results show that extra enzyme in the Master Mix forced "mispriming" to occur (determined by subsequent sequencing). The 1/10, 1/20, and 1/30 dilutions of the Microcon 100 purified bisulfite-treated gDNA still provided enough gDNA template for MSP for almost all of the reactions. Successful PCR was seen even when only 0.2 ng of gDNA was used in MSP. Although there were two data points that "dropped out," overall the data are excellent. Thus, it appears that as little as 0.2 ng of DNA can be used with successful PCR yields.

Studies Using Additional Templates

The studies above included only unmethylated DNA. The following experiments include side by side comparisons of methylated to unmethylated gDNA. Five additional "control" reactions were evaluated with both methylated and unmethylated gDNA. These samples contained 1 µL DNA from Coriell or 3 µL DNA from the Intergen p16 kit (each about 300 ng DNA), 35 µL water, 10 µL 20% Et$_4$NOH, and 85 µL 2M magnesium bisulfite and heated at 50° C. for about 4 hours. The samples were Coriell #34 and #35, and DNA from Intergen's p16 "kit," p16U, p16M, and a universally methylated gDNA. Each was incubated at 50° C. for four hours and subjected to the size-exclusion clean-up method, using a Microcon 100 filtration unit received 50 mL TE. One mL was used in MSP with the following MSP primer pairs: MLH M, MLH U, Dapk M, Dapk U, MgMt M, MgMt U, p16M, and p16U. Excellent MSP yields were obtained as evidence by an amplicon of the correct size, several of the PCRs were subjected to direct sequencing.

The same bisulfite treated samples were additionally analyzed by sequencing with other primers for different gene targets: E2F2, Frap, Xpd, CDKN1C, Ral GDS, Etsl, Cdhl, Apcl, Esrl, MLhl, and CMyc. These primers are:

```
E2F2FwdFam    FAM-GGTTTGGGGAATATATTGTTGGG           (SEQ ID NO:21)
E2F2Rev       CTTAAAAAAACAACCACACCTACTATTAATACC    (SEQ ID NO:22)

Cdh1FwdFam    FAM-TGTGTTTGTAGGAGTTTGTGTTTGTG        (SEQ ID NO:23)
Cdh1Rev       CTCCAAAATCCTCCAAACCC                  (SEQ ID NO:24)

Frap1FwdFam   FAM-GATTGGTTTTTAGGGTTGGGAA            (SEQ ID NO:25)
Frap1Rev      TCCCCTAACCCCCCCTC                     (SEQ ID NO:26)

XpdFwdFam     FAM-GGGTTTGATTAATATTTAATTTTGGTAGG    (SEQ ID NO:27)
XpdRev        TCAATCCACTAAAACACAACCAATC             (SEQ ID NO:28)

CDKN1CfwdFam  FAM-GTTTTATAGGTTAAGTGTGTTGTGTT        (SEQ ID NO:29)
CDRN1Crev     CACTAATACTAAAAAAATCCCACAAAC           (SEQ ID NO:30)

RalGDSFwdFam  FAMGGGTTTTATAGTTTTTGTATTTAGGTTTTTATTG (SEQ ID NO:31)
RalGDSRev     CAACTCAATAAACTCAAACTCCCC              (SEQ ID NO:32)

ID2FwdFam     FAMGAAGGTGAGTAAGATGGAAATTTTGTAGTA    (SEQ ID NO:33)
ID2Rev        ACTAACAATTTCACACACAACTCAATCTAC       (SEQ ID NO:34)
```

-continued

| | | |
|---|---|---|
| Apc1FwdFam | FAM-AGGGAAAATTGGAGTAGGAGGTT | (SEQ ID NO:35) |
| Apc1Rev | ACTCAACTCCCCAAAACTATCCTTAA | (SEQ ID NO:36) |
| Esr1FwdFam | FAM-TGGGAGATTAGTATTTAAAGTTGGAGG | (SEQ ID NO:37) |
| Esr1Rev | CCTTAAATCTAATACAATAAAACCATCCC | (SEQ ID NO:38) |
| Ets1FwdFam | FAM-GGGAATTTGAGATTTTTGGGAAG | (SEQ ID NO:39) |
| Ets1Rev | CCCAACTACCAACAACATCCC | (SEQ ID NO:40) |
| M1h1FwdFam | FAM-GTAGTTTTTTTTTAGGAGTGAAGGAGGT | (SEQ ID NO:41) |
| M1h1Rev | CCCTACTCTTATAACCTCCCACAAAT | (SEQ ID NO:42) |
| CMycFwdFam | FAM-GGGAGGTTATTTTGTTTATTTGGG | (SEQ ID NO:43) |
| CMycRev | CCAAAACCCAAAAAACAATTAACAC | (SEQ ID NO:44) |

Comparison of Magnesium bisulfite/Et$_4$NOH to Sodium Bisulfite Protocol after 6 Hour and 15 Hour Reaction Times A direct comparison between samples prepared according to the sodium bisulfite protocol (J. Herman, *Proc. Natl. Acad. Sci.* 93, 9821-26 (1996)) and the magnesium bisulfite protocol as described in Ex. 10 was conducted, using Et$_4$NOH, NaOH, and no additive. Two plates were set up, one for a 6 hour analysis and the other for a 15 hour analysis. Both reactions took place at 50° C. Only an unmethylated gDNA sample was investigated. All reaction products were purified by the size-exclusion clean-up procedure described above and recovered in a final volume of 50 µL of TE. MSP was used to analyze the converted DNA. The sodium bisulfite procedure provided gDNA that gave excellent results in MSP. The magnesium bisulfite converted gDNA gave much weaker signals in MSP than the sodium bisulfite converted DNA. However, the magnesium bisulfite/Et$_4$NOH differs from the sodium bisulfite protocol in significant ways. The magnesium bisulfite/Et$_4$NOH was achieved without a pre-denaturation step, much lower concentration of bisulfite, no exacting pH control, no antioxidant, and reagents were "off the shelf" and not freshly prepared.

The size-exclusion purification worked well on the sodium bisulfite samples as well as the magnesium bisulfite samples.

Direct Comparison of Magnesium Bisulfite with Et$_4$NOH and Sodium Bisulfite Reactions on Both Methylated and Unmethylated gDNA The 1.3M (final concentration) magnesium bisulfite with Et$_4$NOH reaction was compared to the samples treated with sodium bisulfate, according to the known method. The magnesium bisulfite recipe was 1 µL Coriell or 3 µL Intergen, 32 or 34 µL water, 10 µL 20% Et$_4$NOH, 85 µL 2M magnesium bisulfite. Two methylated samples and two unmethylated samples were compared in side by side reactions with sodium bisulfite and the magnesium bisulfite. These were allowed to react for 6 and 15 hours at 50° C. for a total of sixteen (16) samples processed. Purification by the size-exclusion process described above was performed. In this very thorough comparison, the 16 samples, purified by Microcon 100, were all analyzed by sequencing. (The sequencing analysis allows for all cytosine in a given region to be analyzed for completeness of the bisulfite conversion to uracil.)

Eleven different primer sets for specific gene targets were used: E2F2, FRAP, XPD, CDKN, RalDGS, IDT, CDH1, APC1, and ESR. The results showed that the methods disclosed herein are viable alternatives to the sodium bisulfite reaction. The studies herein utilized 2M magnesium bisulfite solution, which is diluted in the sample to about 1.3M. Use of a more concentrated magnesium bisulfite solution would yield higher bisulfite concentration for conversion, while still keeping reaction volumes to a minimum. Such increased bisulfite concentration in the reaction mixture could easily be employed, and would be expected to enhance PCR yields. The optimization of such reaction parameters, including volume and/or concentration of magnesium bisulfite solution, temperature, pH and other reaction conditions are expected to lead to more complete conversion, and are well within the skill of the art.

Evaluation of HPLC Model System

A model system using a synthetic, four base oligonucleotide, ATCG, was employed to determine the rate of cytosine to uracil conversion by HPLC. Samples contained Et$_4$NOH, no additive, tetramethyl ammonium chloride (TMAC), or guanidine HCl in the magnesium bisulfite reaction. The composition of the samples of Examples 19-22 is shown in Table 5 below.

TABLE 5

| Ex. 19 | Ex. 20 | Ex. 21 | Ex. 22 |
|---|---|---|---|
| ATCG 2.5 µL | ATCG 2.5 µL | ATCG 2.5 µL | ATCG 2.5 µL |
| 2 M Mg(HSO$_3$) 16.3 µL (~1.3 M final) | 2 M Mg(HSO$_3$) 16.3 µL (~1.3 M final) | 2 M Mg(HSO$_3$) 16.3 µL (~1.3 M final) | 2 M Mg(HSO$_3$) 16.3 µL (~1.3 M final) |
| 20% Et$_4$NOH 2 µL | — | TMAC 1.25 µL | 3 M Guanidine HCl 0.83 µL (0.1 M final) |
| Water 4.2 µL pH ~4 | Water 6 µL pH ~3 | Water 4.95 µL pH ~3 | Water 5.4 uL pH ~3-4 |

Each sample was heated at 50° C. for about 28 minutes. The pH of the samples was measured after heating with pH paper, and is therefore approximate. All samples reacted comparably to each other, with the Et$_4$NOH reaction performing slightly better than the others.

Another HPLC study was conducted evaluating Et$_4$NOH, NaOH, Et$_4$NCl, and guanidine thiocyanide as catalysts. The composition of the samples (Examples 23-26) is shown in Table 6, below.

TABLE 6

| Ex. 23 | Ex. 24 | Ex. 25 | Ex. 26 |
|---|---|---|---|
| ATCG 2.5 µL | ATCG 2.5 µL | ATCG 2.5 µL | ATCG 2.5 µL |
| 2 M Mg(HSO$_3$)$_2$ 16.3 Ml (~1.3 M final) | 2 M Mg(HSO$_3$)$_2$ 16.3 µL (~1.3 M final) | 2 M Mg(HSO$_3$)$_2$ 16.3 µL (~1.3 M final) | — |
| 20% Et$_4$NOH 2 µL | 5 M NaOH 0.5 µL | 2 M Et$_4$NCl 2 µL | 2 M guanidine thiocyanide 16.3 uL |
| Water 4.2 µL pH ~3 | Water 5.7 uL pH ~3 | Water 4.2 µL pH ~2 | Water 6.2 uL pH ~4 |

Each sample was heated at 50° C. for about 32 minutes. pH was measured after heating with pH paper, and is therefore approximate. Each of the reactions compared favorably to each other, with the exception of the guanidine thiocyanide reaction, which did not react at all. The Et$_4$NOH reaction provided the beast results, with the NaOH reaction being nearly as effective. The Et$_4$NCl reaction was useable, but was less effective than either the NaOH reaction or the Et$_4$NOH reaction. Thus, pH may be important in the reaction.

Applicants have also discovered that, although they see significant benefits in using magnesium bisulfite instead of sodium bisulfite, significant improvements may also be seen, regardless of which bisulfite is used, with the modified purification processes discussed herein. Processes for purification are further discussed in the application entitled "Improved Bisulfite Method" (U.S. application Ser. No. 10/926,534, filed Aug. 26, 2004 claiming priority to U.S. application Ser. No. 60/498,996 filed Aug. 29, 2003, and also application Ser. No. 60/520,941 (5109P2) having the same title and filed Nov. 17, 2003, now U.S. Pat. No. 7,262,013, issued Aug. 28, 2007) assigned to the Assignee hereof, and which is incorporated by reference in its entirety. One embodiment of that process uses a Microcon 100 (Millipore), or similar, size-exclusion device. According to one embodiment of that method, the sample and 200 µL of water was added to the Microcon 100 device, and the sample was then spun in the device at approximately 2800 RPM for about 8 minutes (as per manufacturers recommendation). The resultant filtrate was removed. Two subsequent washes with about 300 µL water, each spun at about 2800 RPM for 8 minutes followed. After each, the filtrate was again removed. About 300 µL 0.1N NaOH was added and spun at approximately 2800 RPM for about 8 minutes. Again, the filtrate was removed. After addition of about 300 µL of water, the sample was spun in the device at 2800 RPM for about 6-8 minutes. The filtrate was removed and about 50 µL TE buffer was added. After about 5 minutes before it was inverted to collect the purified DNA sample in a centrifuge. Approximately 60 µL were collected.

While the above-described methods of PCR and sequencing are currently preferred, they are not the only methods useable. The present invention is not limited to these particular embodiments, or any of the examples above. Rather, other variants of these methods will be apparent to those skilled in the art and are within the scope and spirit of the invention disclosed herein.

What is claimed is:

1. A method for converting cytosine to uracil comprising the steps of:
   providing a nucleic acid comprising at least one cytosine nucleobase; and
   reacting said nucleic acid with a bisulfite ion, in the presence of a quaternary amine catalyst having the Formula:

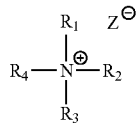

or a derivative thereof, wherein:
   $R_1$, $R_2$, $R_3$ and $R_4$ are each independently $C_1$-$C_4$ alkyl; and
   Z is selected from halides and OH.

2. The method of claim 1, wherein said quaternary amine catalyst comprises a quaternary alkyl ammonium compound.

3. The method of claim 1, wherein said quaternary amine catalyst comprises a quaternary alkyl ammonium salt.

4. The method of claim 1, wherein said quaternary amine catalyst comprises a quaternary alkyl ammonium halide.

5. The method of claim 1, wherein said quaternary amine catalyst comprises a quaternary ammonium chloride or a quaternary ammonium bromide.

6. The method of claim 1, wherein said quaternary amine catalyst comprises at least one of quaternary methyl ammonium bromide, tetraethylammonium hydroxide, tetraethylammonium chloride, tetrabutylammonium chloride and tetrabutylammonium bromide.

7. The method of claim 1, wherein said catalyst comprises tetraethylammonium hydroxide.

8. The method of claim 1, wherein said reaction is performed in a solution containing bisulfite ion in a concentration of from about 0.5M to about 2M.

9. The method of claim 8, wherein said solution contains bisulfite ion in a concentration of about 1M to about 2M.

10. The method of claim 1, wherein said reaction is performed in a solution containing magnesium bisulfite in a concentration of from about 0.5M to about 2M.

11. The method of claim 10, wherein said solution contains magnesium bisulfite in a concentration of about 1M to about 2M.

12. The method of claim 5, wherein said reaction is performed in a solution containing magnesium bisulfite in a concentration of from about 0.5M to about 2M.

13. The method of claim 7, wherein said reaction is performed in a solution containing magnesium bisulfite in a concentration of from about 0.5M to about 2M.

14. The method of claim 3, wherein said reaction is performed in a solution containing magnesium bisulfite in a concentration of from about 0.5M to about 2.5M.

15. The method of claim 1, wherein said bisulfite solution comprises magnesium bisulfite having a concentration of at least about 1M.

16. A method for conversion of cytosine to uracil comprising the steps of:
   reacting a DNA sample in solution with a bisulfite ion and quaternary amine catalyst having the Formula:

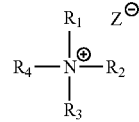

or a derivative thereof wherein:
   $R_1$, $R_2$, $R_3$ and $R_4$ each independently $C_1$-$C_4$ alkyl; and
   Z is selected from halides and OH and,
   wherein the final concentration of bisulfite is at least from about 1M to about 3M.

17. The method of claim 16, wherein said final concentration of said bisulfite is about 1.3M.

18. The method of claim 16, wherein said reaction is performed at about 50 degrees for about 4 to about 15 hours.

19. The method of claim 16, wherein said bisulfite salt comprises magnesium bisulfite, and said quaternary amine catalyst comprises tetraethylaxnmonium hydroxide.

20. The method of claim 19, wherein said reaction is performed at about 50 degrees for about 4 to about 15 hours.

21. The method of claim 1, wherein said nucleic acid is gDNA.

22. The method of claim 1, further comprising treating the product of said reaction of said nucleic acid and said bisulfite ion with a base.

23. The method of claim 22, wherein said base is NaOH.

* * * * *

SEQUENCE LISTING

```
<160> NUMBER OF SEQ ID NOS: 44

<210> SEQ ID NO 1
<211> LENGTH: 24
<212> TYPE: DNA
<213> ORGANISM: Artificial Sequence
<220> FEATURE:
<223> OTHER INFORMATION: sense

<400> SEQUENCE: 1
ttattagagg gtggggtgga ttgt                                          24

<210> SEQ ID NO 2
<211> LENGTH: 22
<212> TYPE: DNA
<213> ORGANISM: Artificial Sequence
<220> FEATURE:
<223> OTHER INFORMATION: antisense

<400> SEQUENCE: 2
caaccccaaa ccacaaccat aa                                            22

<210> SEQ ID NO 3
<211> LENGTH: 24
<212> TYPE: DNA
<213> ORGANISM: Artificial Sequence
<220> FEATURE:
<223> OTHER INFORMATION: sense

<400> SEQUENCE: 3
ttattagagg gtggggcgga tcgc                                          24

<210> SEQ ID NO 4
<211> LENGTH: 21
<212> TYPE: DNA
<213> ORGANISM: Artificial Sequence
<220> FEATURE:
<223> OTHER INFORMATION: antisense

<400> SEQUENCE: 4
```
gaccccgaac cgcgaccgta a                    21

<210> SEQ ID NO 5
<211> LENGTH: 29
<212> TYPE: DNA
<213> ORGANISM: Artificial Sequence
<220> FEATURE:
<223> OTHER INFORMATION: sense

<400> SEQUENCE: 5
tttgtgtttt gatgtttgta ggtttttgt            29

<210> SEQ ID NO 6
<211> LENGTH: 28
<212> TYPE: DNA
<213> ORGANISM: Artificial Sequence
<220> FEATURE:
<223> OTHER INFORMATION: antisense

<400> SEQUENCE: 6
aactccacac tcttccaaaa acaaaaca             28

<210> SEQ ID NO 7
<211> LENGTH: 23
<212> TYPE: DNA
<213> ORGANISM: Artificial Sequence
<220> FEATURE:
<223> OTHER INFORMATION: sense

<400> SEQUENCE: 7
tttcgacgtt cgtaggtttt cgc                  23

<210> SEQ ID NO 8
<211> LENGTH: 22
<212> TYPE: DNA
<213> ORGANISM: Artificial Sequence
<220> FEATURE:
<223> OTHER INFORMATION: antisense

<400> SEQUENCE: 8
gcactcttcc gaaaacgaaa cg                   22

<210> SEQ ID NO 9
<211> LENGTH: 27
<212> TYPE: DNA
<213> ORGANISM: Artificial Sequence
<220> FEATURE:
<223> OTHER INFORMATION: sense

<400> SEQUENCE: 9
ggaggatagt tggattgagt taatgtt              27

<210> SEQ ID NO 10
<211> LENGTH: 20
<212> TYPE: DNA
<213> ORGANISM: Artificial Sequence
<220> FEATURE:
<223> OTHER INFORMATION: antisense

<400> SEQUENCE: 10
caatccctcc caaacaccaa                      20

<210> SEQ ID NO 11
<211> LENGTH: 24
<212> TYPE: DNA
<213> ORGANISM: Artificial Sequence

```
<220> FEATURE:
<223> OTHER INFORMATION: sense

<400> SEQUENCE: 11
ggatagtcgg atcgagttaa cgtc                                        24

<210> SEQ ID NO 12
<211> LENGTH: 15
<212> TYPE: DNA
<213> ORGANISM: Artificial Sequence
<220> FEATURE:
<223> OTHER INFORMATION: antisense

<400> SEQUENCE: 12
ccctcccaaa cgccg                                                  15

<210> SEQ ID NO 13
<211> LENGTH: 29
<212> TYPE: DNA
<213> ORGANISM: Artificial Sequence
<220> FEATURE:
<223> OTHER INFORMATION: sense

<400> SEQUENCE: 13
ttttgatgta gatgttttat tagggttgt                                   29

<210> SEQ ID NO 14
<211> LENGTH: 24
<212> TYPE: DNA
<213> ORGANISM: Artificial Sequence
<220> FEATURE:
<223> OTHER INFORMATION: antisense

<400> SEQUENCE: 14
accacctcat cataactacc caca                                        24

<210> SEQ ID NO 15
<211> LENGTH: 24
<212> TYPE: DNA
<213> ORGANISM: Artificial Sequence
<220> FEATURE:
<223> OTHER INFORMATION: sense

<400> SEQUENCE: 15
acgtagacgt tttattaggg tcgc                                        24

<210> SEQ ID NO 16
<211> LENGTH: 20
<212> TYPE: DNA
<213> ORGANISM: Artificial Sequence
<220> FEATURE:
<223> OTHER INFORMATION: antisense

<400> SEQUENCE: 16
cctcatcgta actacccgcg                                             20

<210> SEQ ID NO 17
<211> LENGTH: 25
<212> TYPE: DNA
<213> ORGANISM: Artificial Sequence
<220> FEATURE:
<223> OTHER INFORMATION: sense

<400> SEQUENCE: 17
tgtgatgtgt ttgtattttg tggtt                                       25
```

<210> SEQ ID NO 18
<211> LENGTH: 23
<212> TYPE: DNA
<213> ORGANISM: Artificial Sequence
<220> FEATURE:
<223> OTHER INFORMATION: antisense

<400> SEQUENCE: 18
ccatacaata accaaacaac caa                                        23

<210> SEQ ID NO 19
<211> LENGTH: 19
<212> TYPE: DNA
<213> ORGANISM: Artificial Sequence
<220> FEATURE:
<223> OTHER INFORMATION: sense

<400> SEQUENCE: 19
gcgttcgtat tttgcggtt                                             19

<210> SEQ ID NO 20
<211> LENGTH: 22
<212> TYPE: DNA
<213> ORGANISM: Artificial Sequence
<220> FEATURE:
<223> OTHER INFORMATION: antisense

<400> SEQUENCE: 20
cgtacaataa ccgaacgacc ga                                         22

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
ggtttgggga atatattgtt ggg                                        23

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
cttaaaaaaa caaccacacc tactattaat acc                             33

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
tgtgtttgta ggagtttgtg tttgtg                                     26

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctccaaaatc ctccaaaccc                                                     20

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
gattggtttt tagggttggg aa                                                  22

<210> SEQ ID NO 26
<211> LENGTH: 17
<212> TYPE: DNA
<213> ORGANISM: Artificial Sequence
<220> FEATURE:
<223> OTHER INFORMATION: primer

<400> SEQUENCE: 26
tcccctaacc cccctc                                                         17

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
gggtttgatt aatatttaat tttggtagg                                           29

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
tcaatccact aaaacacaac caatc                                               25

<210> SEQ ID NO 29
<211> LENGTH: 26
<212> TYPE: DNA
<213> ORGANISM: Artificial Sequence
<220> FEATURE:
<223> OTHER INFORMATION: primer

<400> SEQUENCE: 29
gttttatagg ttaagtgtgt tgtgtt                                              26

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
cactaatact aaaaaaatcc cacaaac                                             27

<210> SEQ ID NO 31

```
<211> LENGTH: 34
<212> TYPE: DNA
<213> ORGANISM: Artificial Sequence
<220> FEATURE:
<223> OTHER INFORMATION: primer

<400> SEQUENCE: 31
gggttttata gttttttgtat ttaggttttt attg                                34

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
caactcaata aactcaaact cccc                                            24

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
gaaggtgagt aagatggaaa ttttgtagta                                      30

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
actaacaatt tcacacacaa ctcaatctac                                      30

<210> SEQ ID NO 35
<211> LENGTH: 23
<212> TYPE: DNA
<213> ORGANISM: Artificial Sequence
<220> FEATURE:
<223> OTHER INFORMATION: primer

<400> SEQUENCE: 35
agggaaaatt ggagtaggag gtt                                             23

<210> SEQ ID NO 36
<211> LENGTH: 26
<212> TYPE: DNA
<213> ORGANISM: Artificial Sequence
<220> FEATURE:
<223> OTHER INFORMATION: primer

<400> SEQUENCE: 36
actcaactcc ccaaaactat ccttaa                                          26

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
```
tgggagatta gtatttaaag ttggagg                                              27

<210> SEQ ID NO 38
<211> LENGTH: 29
<212> TYPE: DNA
<213> ORGANISM: Artificial Sequence
<220> FEATURE:
<223> OTHER INFORMATION: primer

<400> SEQUENCE: 38
ccttaaatct aatacaataa aaccatccc                                            29

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
gggaatttga gattttggg aag                                                   23

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
cccaactacc aacaacatcc c                                                    21

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
gtagtttttt ttttaggagt gaaggaggt                                            29

<210> SEQ ID NO 42
<211> LENGTH: 26
<212> TYPE: DNA
<213> ORGANISM: Artificial Sequence
<220> FEATURE:
<223> OTHER INFORMATION: primer

<400> SEQUENCE: 42
ccctactctt ataacctccc acaaat                                               26

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
gggaggttat tttgtttatt tggg                                                 24

<210> SEQ ID NO 44
<211> LENGTH: 25
<212> TYPE: DNA

```
<213> ORGANISM: Artificial Sequence
<220> FEATURE:
<223> OTHER INFORMATION: primer

<400> SEQUENCE: 44
ccaaaaccca aaaaacaatt aacac                                              25
```